(12) United States Patent
Scott et al.

(10) Patent No.: US 12,035,941 B2
(45) Date of Patent: Jul. 16, 2024

(54) AIRFLOW CHANNELS AND PATTERNS IN LUMEN FOR CANNULA

(71) Applicant: Cilag GmbH International, Zug (CH)

(72) Inventors: Gregory G. Scott, Cincinnati, OH (US); Jeffrey L. Savage, West Chester, OH (US)

(73) Assignee: Cilag GmbH International, Zug (CH)

(*) Notice: Subject to any disclaimer, the term of this patent is extended or adjusted under 35 U.S.C. 154(b) by 348 days.

(21) Appl. No.: 17/213,508

(22) Filed: Mar. 26, 2021

(65) Prior Publication Data

US 2021/0338278 A1 Nov. 4, 2021

Related U.S. Application Data

(60) Provisional application No. 63/018,660, filed on May 1, 2020.

(51) Int. Cl.
*A61B 17/34* (2006.01)
*A61M 13/00* (2006.01)

(52) U.S. Cl.
CPC ...... *A61B 17/3462* (2013.01); *A61B 17/3423* (2013.01); *A61M 13/003* (2013.01); *A61B 2017/3482* (2013.01)

(58) Field of Classification Search
CPC ............ A61B 17/3462; A61B 17/3423; A61B 2017/3482; A61B 17/3474; A61B 17/3421; A61M 13/003
See application file for complete search history.

(56) References Cited

U.S. PATENT DOCUMENTS

| 4,699,616 A | 10/1987 | Nowak et al. |
| 5,147,316 A | 9/1992 | Castillenti |

(Continued)

FOREIGN PATENT DOCUMENTS

| AU | 702882 B2 | 3/1993 |
| CN | 106344126 B | 2/2019 |

(Continued)

OTHER PUBLICATIONS

International Search Report and Written Opinion dated Jul. 22, 2021, for International Application No. PCT/EP2021/061421, 15 pages.

(Continued)

*Primary Examiner* — Darwin P Erezo
*Assistant Examiner* — Brigid K Byrd
(74) *Attorney, Agent, or Firm* — Frost Brown Todd LLP

(57) ABSTRACT

A surgical access device includes a proximal end portion configured to support a seal assembly having an insufflation port. The device includes a cannula tube extending distally from the proximal end portion and having an inner surface that defines a lumen extending longitudinally through the cannula tube. The cannula tube is configured to be inserted distally through a body cavity wall of a patient, and the lumen is configured to guide a surgical instrument shaft distally through the cannula tube for accessing a body cavity of the patient. The device includes a channel formed in the inner surface of the cannula tube. The channel extends longitudinally between a proximal end of the lumen and a distal end of the lumen, and the channel is configured to direct a gas therethrough to or from the insufflation port of the seal assembly while a surgical instrument shaft is disposed within the lumen.

20 Claims, 16 Drawing Sheets

(56) References Cited

U.S. PATENT DOCUMENTS

| | | | |
|---|---|---|---|
| 5,215,531 A | 6/1993 | Maxson et al. | |
| 5,256,147 A | 10/1993 | Vidal et al. | |
| 5,263,939 A | 11/1993 | Wortrich | |
| 5,267,970 A | 12/1993 | Chin et al. | |
| 5,364,372 A | 11/1994 | Danks et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 6,620,173 B2 | 9/2003 | Gerbi et al. | |
| 6,638,265 B1 | 10/2003 | Ternamian | |
| 7,473,220 B2 | 1/2009 | Francese et al. | |
| 7,614,401 B2 | 11/2009 | Thompson | |
| 7,874,982 B2 | 1/2011 | Selover et al. | |
| 7,981,092 B2 | 7/2011 | Duke | |
| 8,226,553 B2 | 7/2012 | Shelton, IV et al. | |
| 8,251,900 B2 | 8/2012 | Ortiz et al. | |
| 8,435,174 B2 | 5/2013 | Cropper | |
| 8,479,969 B2 | 7/2013 | Shelton, IV | |
| 8,491,533 B2 | 7/2013 | Parihar et al. | |
| 8,551,049 B2 | 10/2013 | Ott et al. | |
| 8,551,050 B2 | 10/2013 | Ott et al. | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,608,715 B2 | 12/2013 | Roberts et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 8,821,527 B2 | 9/2014 | Farnan et al. | |
| 9,113,951 B2 | 8/2015 | Richard et al. | |
| 9,289,200 B2 | 3/2016 | Dang et al. | |
| 9,675,379 B2 | 3/2017 | Kucklick | |
| 10,327,809 B2 | 6/2019 | Buyda et al. | |
| 10,426,873 B2 | 10/2019 | Schultz | |
| 10,792,069 B2 | 10/2020 | Hall et al. | |
| 10,820,924 B2 | 11/2020 | Hall et al. | |
| 11,039,586 B2 | 6/2021 | Yaffe et al. | |
| 11,559,329 B2 | 1/2023 | Scott | |
| 2007/0185380 A1* | 8/2007 | Kucklick | A61B 1/00135 |
| | | | 600/156 |
| 2009/0182282 A1 | 7/2009 | Okihisa et al. | |
| 2010/0010449 A1 | 1/2010 | Leibowitz et al. | |
| 2012/0123216 A1* | 5/2012 | Winfree | A61B 17/3415 |
| | | | 600/208 |
| 2013/0060084 A1 | 3/2013 | Fouts et al. | |
| 2013/0116510 A1 | 5/2013 | Lutze et al. | |
| 2014/0066953 A1 | 3/2014 | Keating et al. | |
| 2014/0371763 A1* | 12/2014 | Poll | A61B 34/30 |
| | | | 606/130 |
| 2015/0087913 A1 | 3/2015 | Dang et al. | |
| 2016/0015423 A1 | 1/2016 | Ravikumar et al. | |
| 2017/0245889 A1 | 8/2017 | Herrell et al. | |
| 2017/0303964 A1 | 10/2017 | Kellner et al. | |
| 2018/0199959 A1 | 7/2018 | Lee | |
| 2018/0206883 A1 | 7/2018 | McIntyre et al. | |
| 2018/0228510 A1 | 8/2018 | Holsten et al. | |
| 2019/0000496 A1 | 1/2019 | Shelton, IV et al. | |
| 2019/0223901 A1* | 7/2019 | Druma | A61B 17/8855 |
| 2019/0380742 A1 | 12/2019 | Hall et al. | |
| 2020/0001025 A1* | 1/2020 | Geisz | A61B 17/3474 |
| 2021/0338269 A1 | 11/2021 | Scott et al. | |
| 2021/0338272 A1 | 11/2021 | Muthuchidambaram et al. | |
| 2021/0338273 A1 | 11/2021 | Vijayachandran et al. | |
| 2021/0338274 A1 | 11/2021 | Scott et al. | |
| 2021/0338275 A1 | 11/2021 | Vijayachandran | |
| 2021/0338276 A1 | 11/2021 | Scott | |
| 2021/0338281 A1 | 11/2021 | Mozloom, Jr. et al. | |
| 2021/0338282 A1 | 11/2021 | Vijayachandran | |
| 2021/0338283 A1 | 11/2021 | McLain | |
| 2021/0338371 A1 | 11/2021 | Harris et al. | |
| 2023/0082376 A1* | 3/2023 | Warner | A61B 1/00135 |
| | | | 600/206 |

FOREIGN PATENT DOCUMENTS

| | | |
|---|---|---|
| DE | 202007001745 U1 | 4/2007 |
| EP | 1884210 A2 | 2/2008 |
| EP | 2174602 A1 | 4/2010 |
| KR | 2016 0017996 A | 2/2016 |
| WO | WO 1999/052457 A1 | 10/1999 |
| WO | WO 2012/128826 A2 | 9/2012 |
| WO | WO 2013/012368 A1 | 1/2013 |
| WO | WO 2014/137530 A1 | 9/2014 |
| WO | WO 2015/049391 A1 | 4/2015 |
| WO | WO 2017/132004 A1 | 8/2017 |
| WO | WO 2018/013734 A1 | 1/2018 |
| WO | WO 2020/036497 A1 | 2/2020 |
| WO | WO 2020/036498 A1 | 2/2020 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.

International Search Report and Written Opinion dated Jul. 16, 2021, for International Application No. PCT/EP2021/061442, 13 pages.

International Search Report and Written Opinion dated Jul. 8, 2021, for International Application No. PCT/EP2021/061447, 15 pages.

International Search Report and Written Opinion dated Jul. 27, 2021, for International Application No. PCT/EP2021/061456, 14 pages.

International Search Report and Written Opinion dated Jul. 13, 2021, for International Application No. PCT/EP2021/061459, 16 pages.

International Search Report and Written Opinion dated Jul. 20, 2021, for International Application No. PCT/EP2021/061466, 17 pages.

International Search Report and Written Opinion dated Jul. 15, 2021, for International Application No. PCT/EP2021/061468, 16 pages.

U.S. Appl. No. 18/077,326.

International Search Report and Written Opinion dated Aug. 3, 2021, for International Application No. PCT/EP2021/061437, 17 pages.

International Search Report and Written Opinion dated Aug. 3, 2021, for International Application No. PCT/EP2021/061460, 12 pages.

* cited by examiner

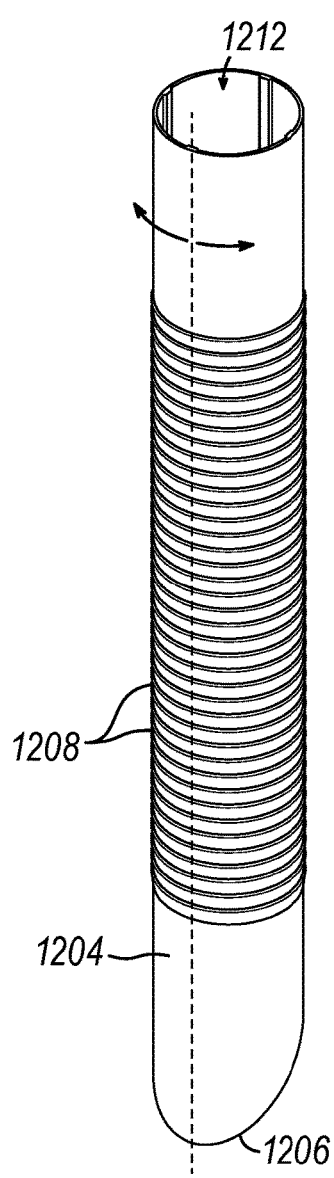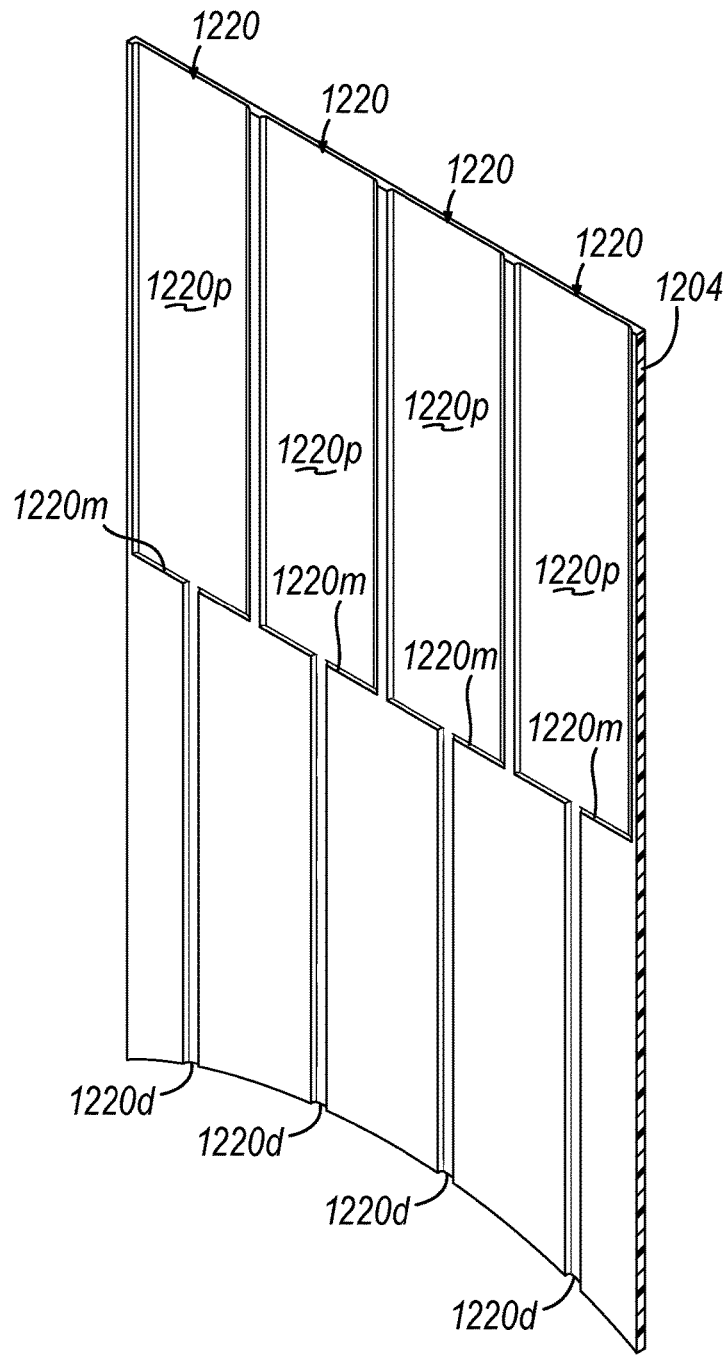
FIG. 20A
FIG. 20B

AIRFLOW CHANNELS AND PATTERNS IN LUMEN FOR CANNULA

PRIORITY

This application claims priority to U.S. Provisional Patent App. No. 63/018,660, entitled "Airflow Channels and Patterns in Lumen for Cannula," filed May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 20A depicts a perspective view of the cannula tube of FIG. 19, showing a hypothetical cut line positioned along an outer surface of the cannula tube;

FIG. 20B depicts a perspective view of the cannula tube of FIG. 19 in a hypothetical-only configuration in which the cannula tube has been cut along the cut line of FIG. 20A and unraveled in the directions indicated in FIG. 20A, showing additional detail of the stepped gas flow channels.

Figure 1:
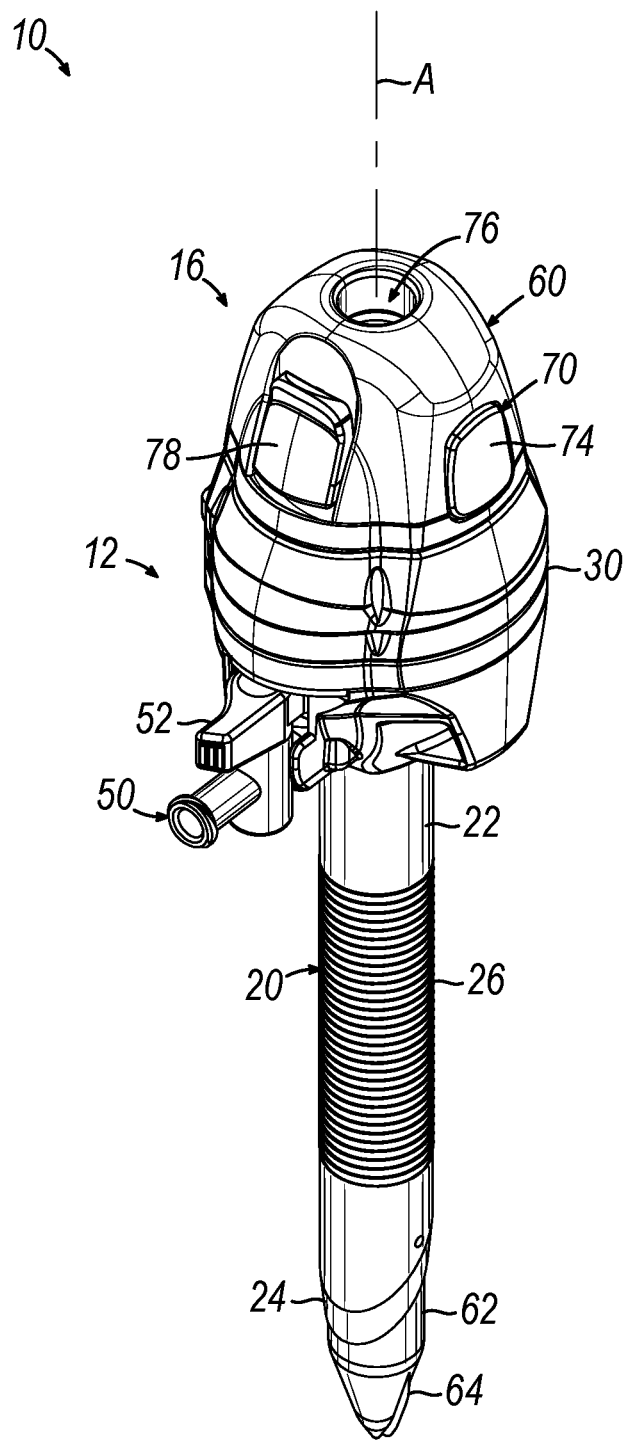
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
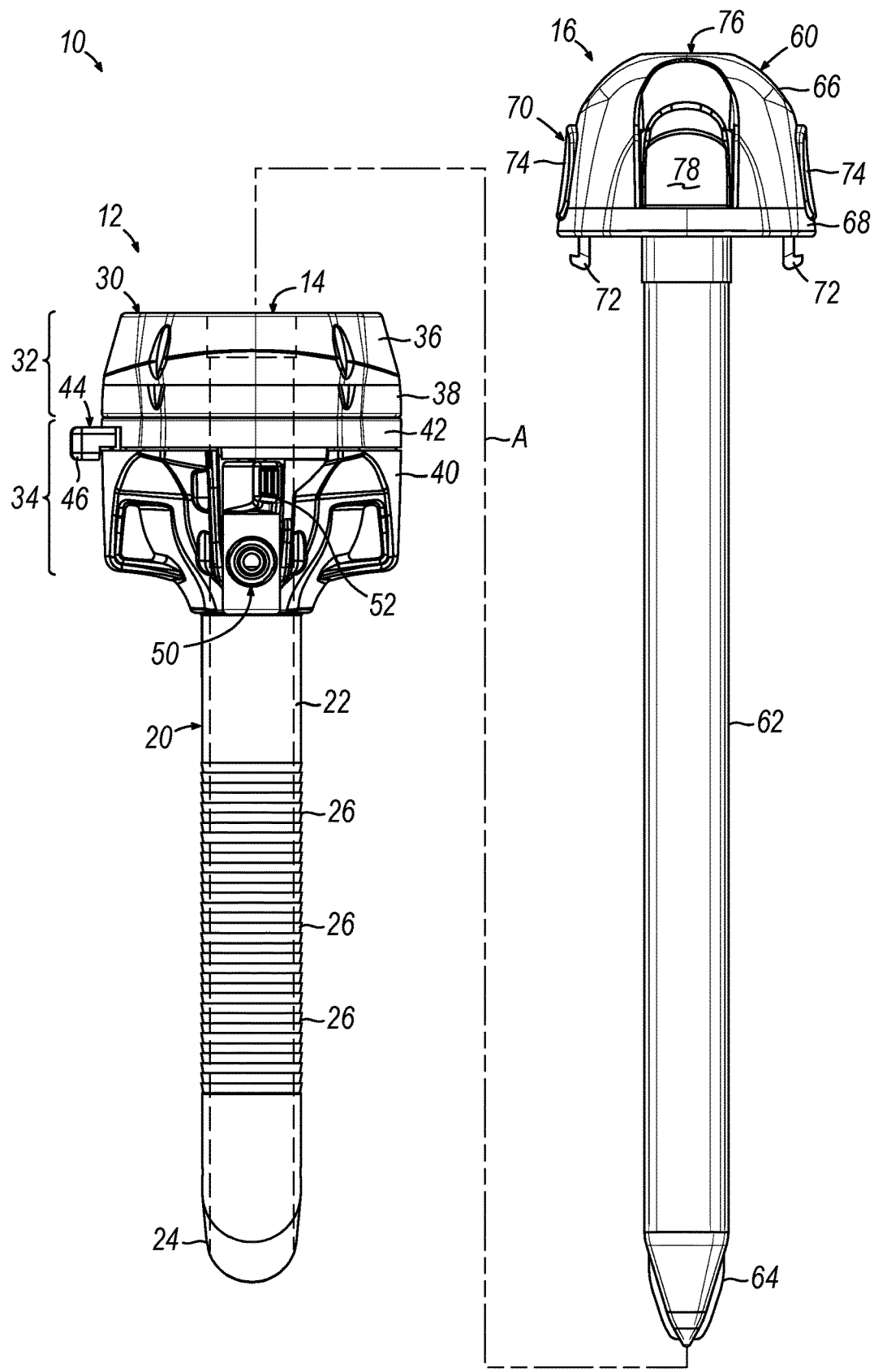
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
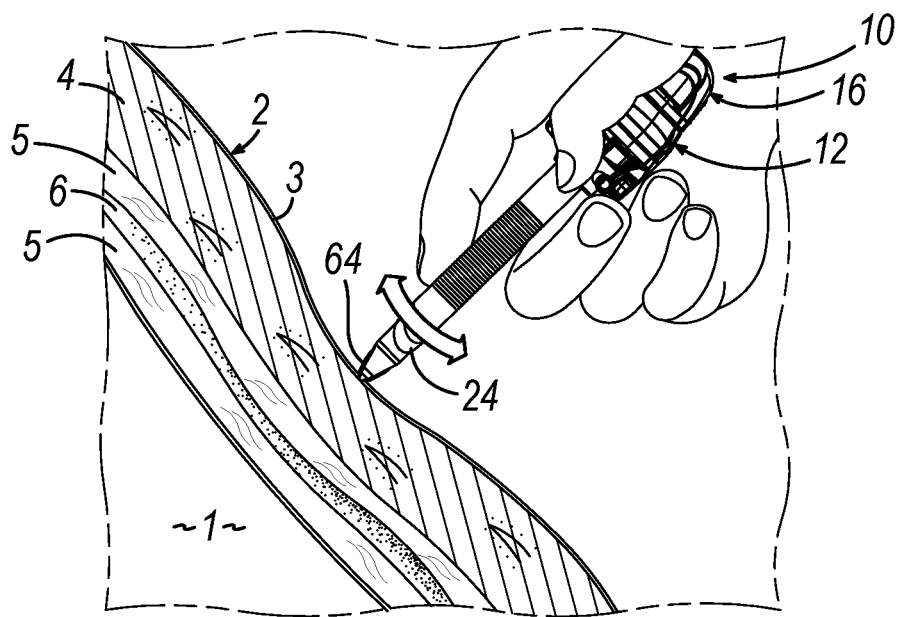
FIG. 3A depicts a side sectional view of the trocar of FIG. 1 being manipulated by a clinician through tissue layers of an abdominal wall.
Figure 3B:
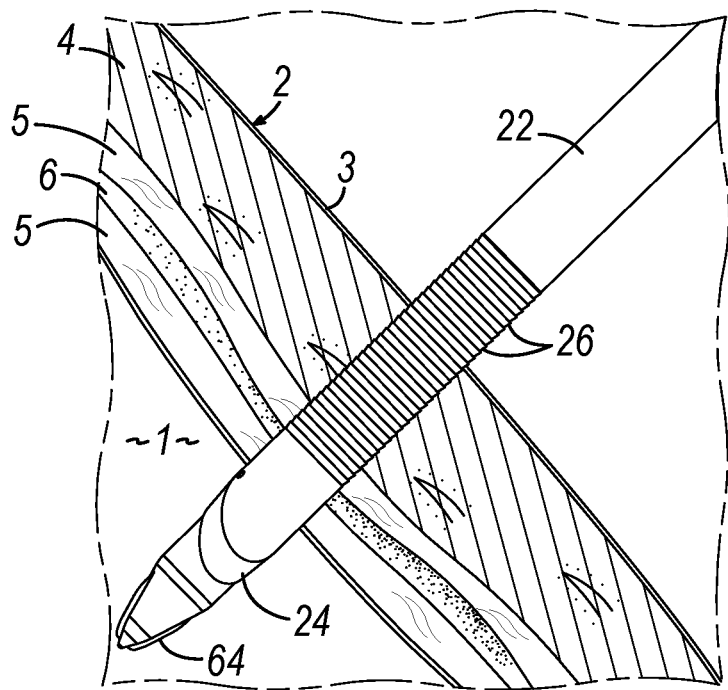
FIG. 3B depicts an enlarged side sectional view of the trocar of FIG. 1, showing a distal end of the trocar received within the abdominal cavity of FIG. 3A.
Figure 3C:
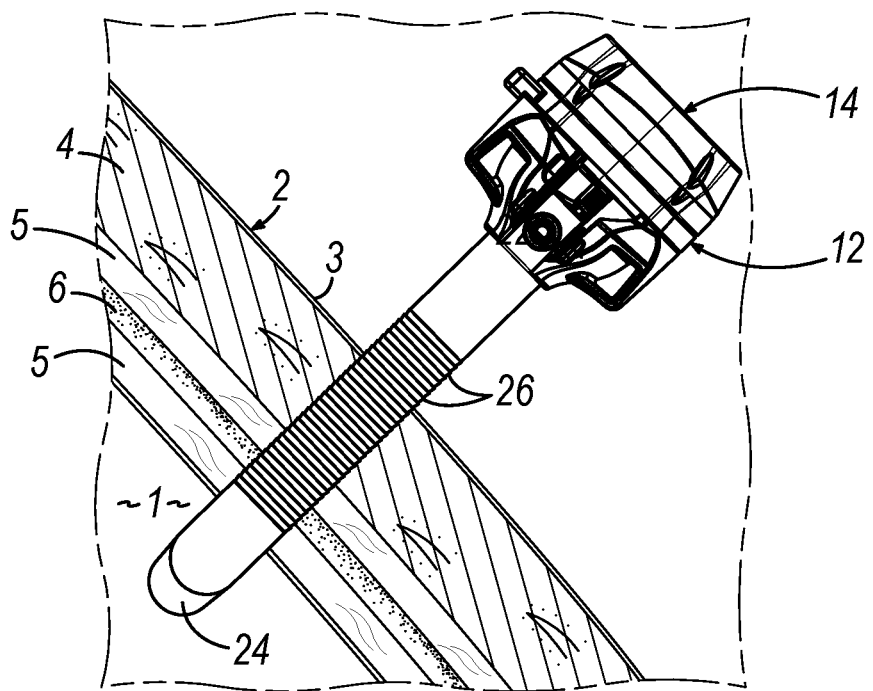
FIG. 3C depicts a side sectional view of the cannula assembly of FIG. 1, showing the cannula assembly remaining positioned within the abdominal wall of FIG. 3A following detachment and removal of the obturator.
Figure 3D:
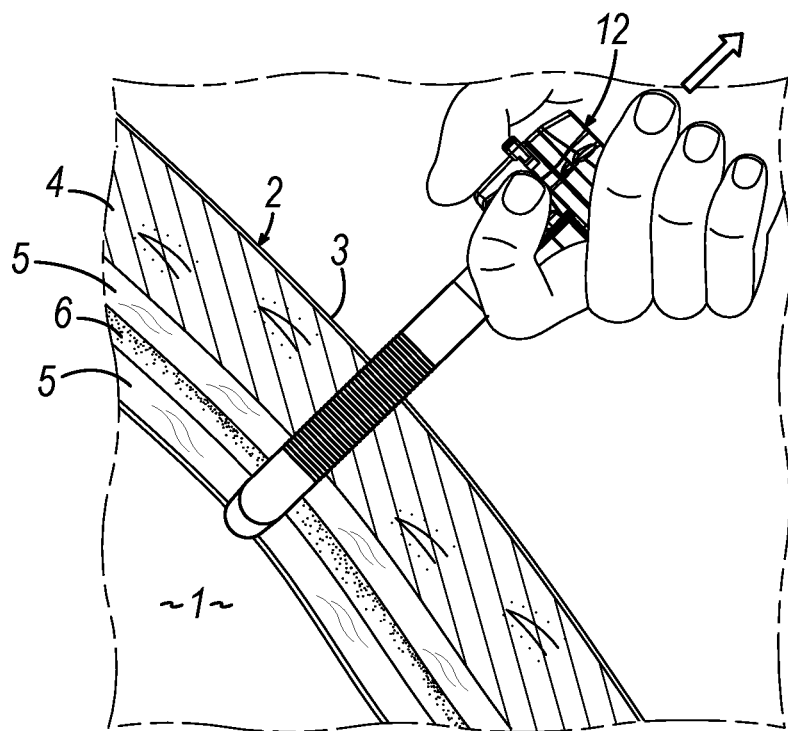
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
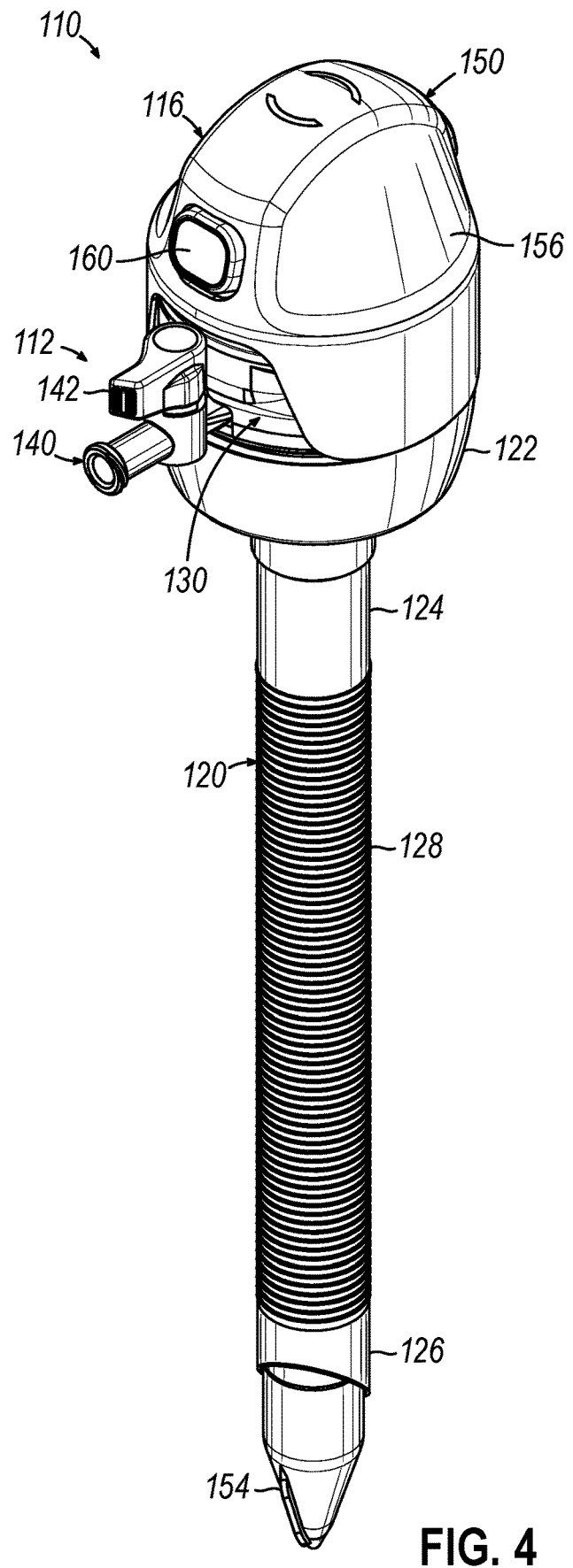
FIG. 4 depicts a perspective view of another exemplary trocar having a cannula assembly and an obturator shown in an assembled state.
Figure 5:
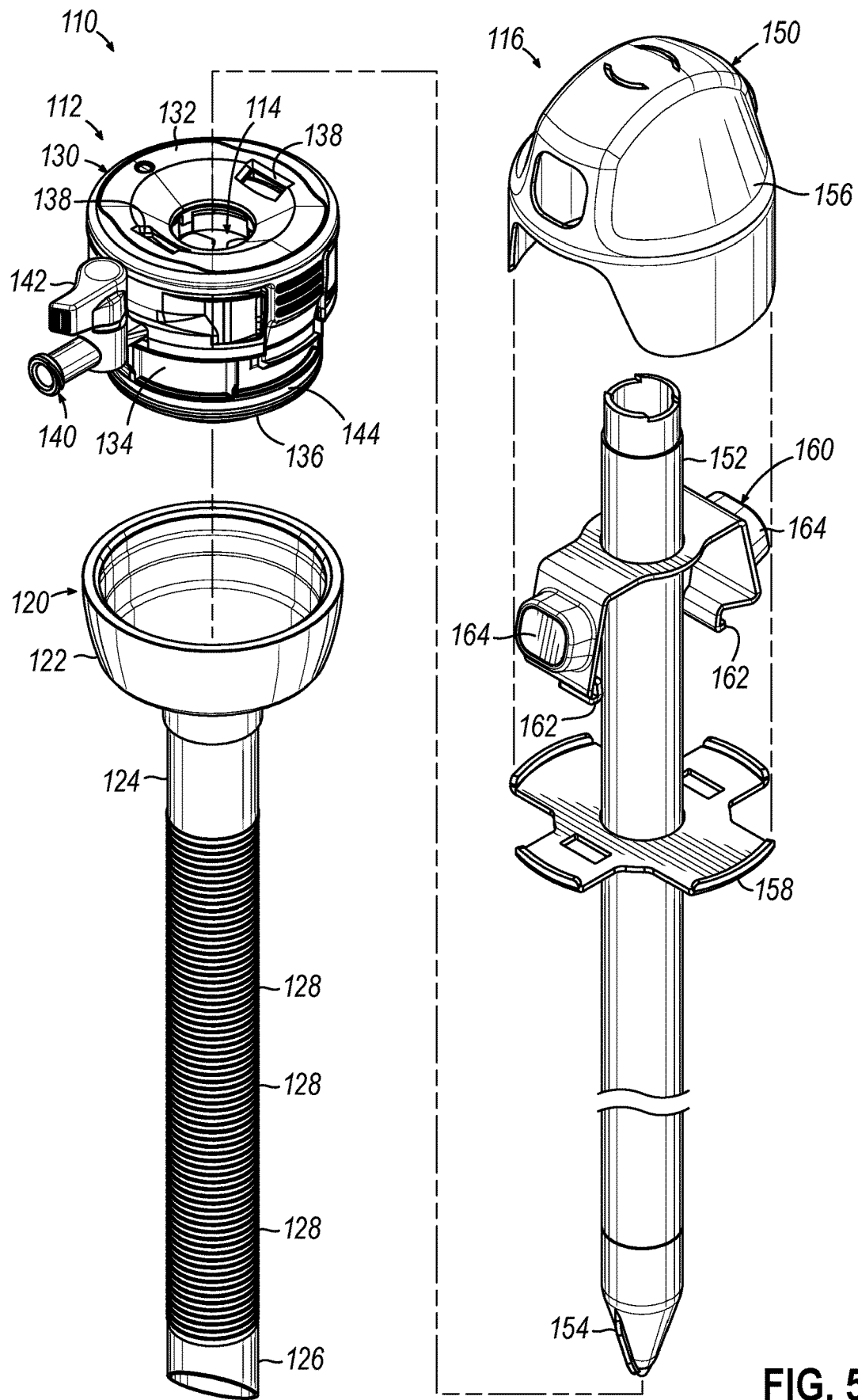
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Cannula Having Integrated Gas Flow Channels

Some laparoscopic surgical procedures include use of electrosurgery instruments to apply radio frequency (RF) energy to tissue to thereby cut and seal the tissue, electrocautery instruments to apply thermal energy to tissue to thereby cauterize the tissue, ultrasonic instruments to apply ultrasonic energy to tissue to thereby seal and/or cut the tissue, or other instruments that apply energy to tissue. Use of such instruments may generate smoke within the abdominal cavity (1) of the patient. Unless properly evacuated from the abdominal cavity (1), such smoke may collect and eventually obscure the surgeon's ability to visualize the surgical site via one or more endoscopes (not shown) positioned within the abdominal cavity (1).

During such procedures in which a surgical instrument having a shaft of a relatively larger diameter is positioned within the working channel (14, 114) of cannula assembly (12, 112), smoke within the abdominal cavity (1) may be at least partially obstructed by the instrument shaft from passing proximally through the cannula lumen and outwardly through insufflation port (50, 140). This results in the undesirable vision obscurity condition discussed above. Accordingly, it may be desirable to provide cannula (20, 120) with a feature that facilitates smoke evacuation from the abdominal cavity (1) when an instrument shaft of relatively larger diameter is positioned within the cannula lumen. It may also be desirable for such a feature to facilitate maintenance of an insufflated state of abdominal cavity (1) while such an instrument shaft of relatively larger diameter is positioned with the cannula lumen.

It will be appreciated that the exemplary gas flow channel features described below in connection with FIGS. 6-21 may be applied to disposable single-use cannulas and sterilizable multi-use cannulas alike, such as cannulas (20, 120) described above.

A. Cannula Having Gas Flow Channels of Uniform Width

Figure 6:
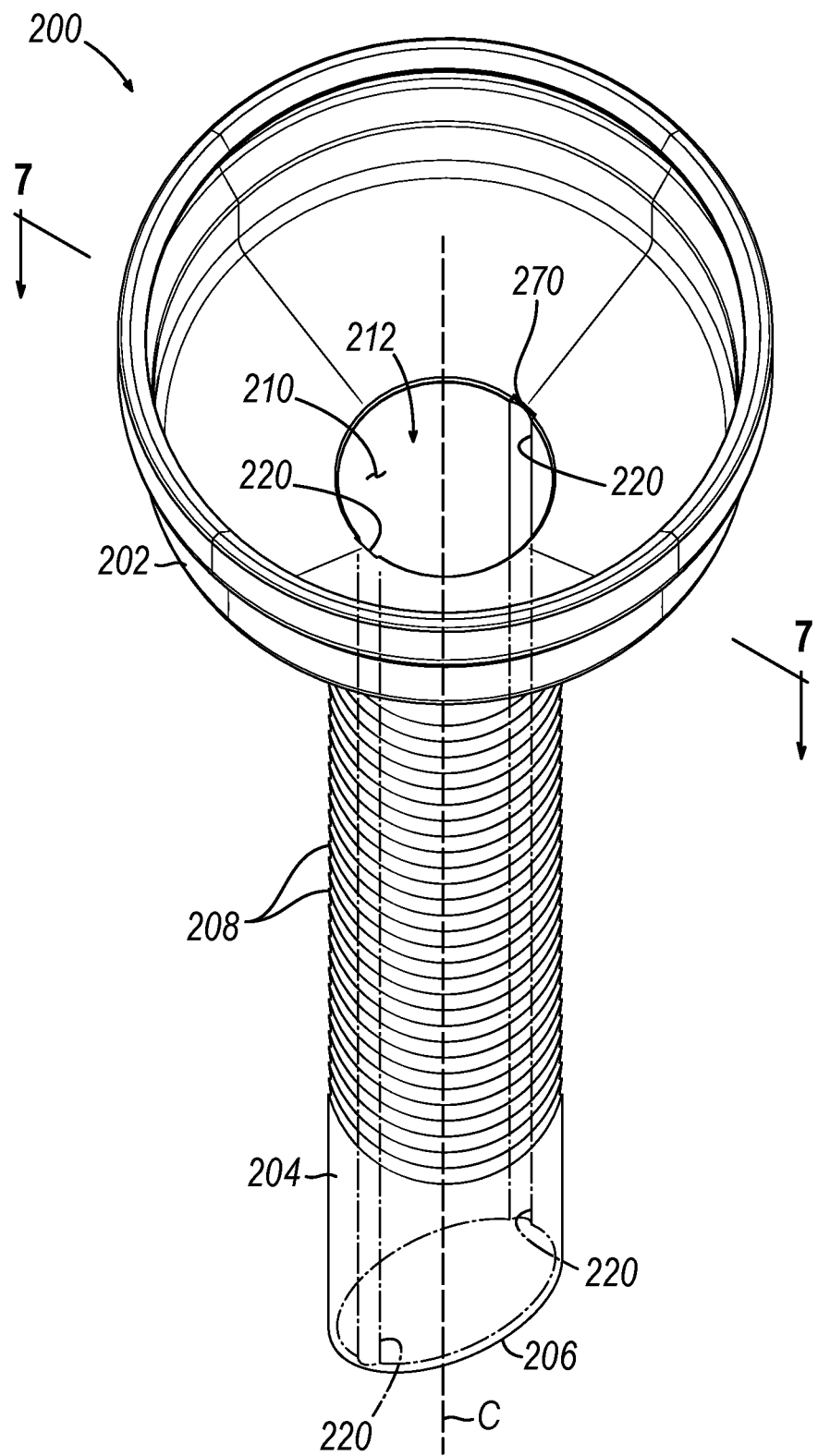
FIG. 6 depicts a perspective view of an exemplary cannula having a pair of gas flow channels formed in a cylindrical inner surface of a tube of the cannula.
Figure 7:
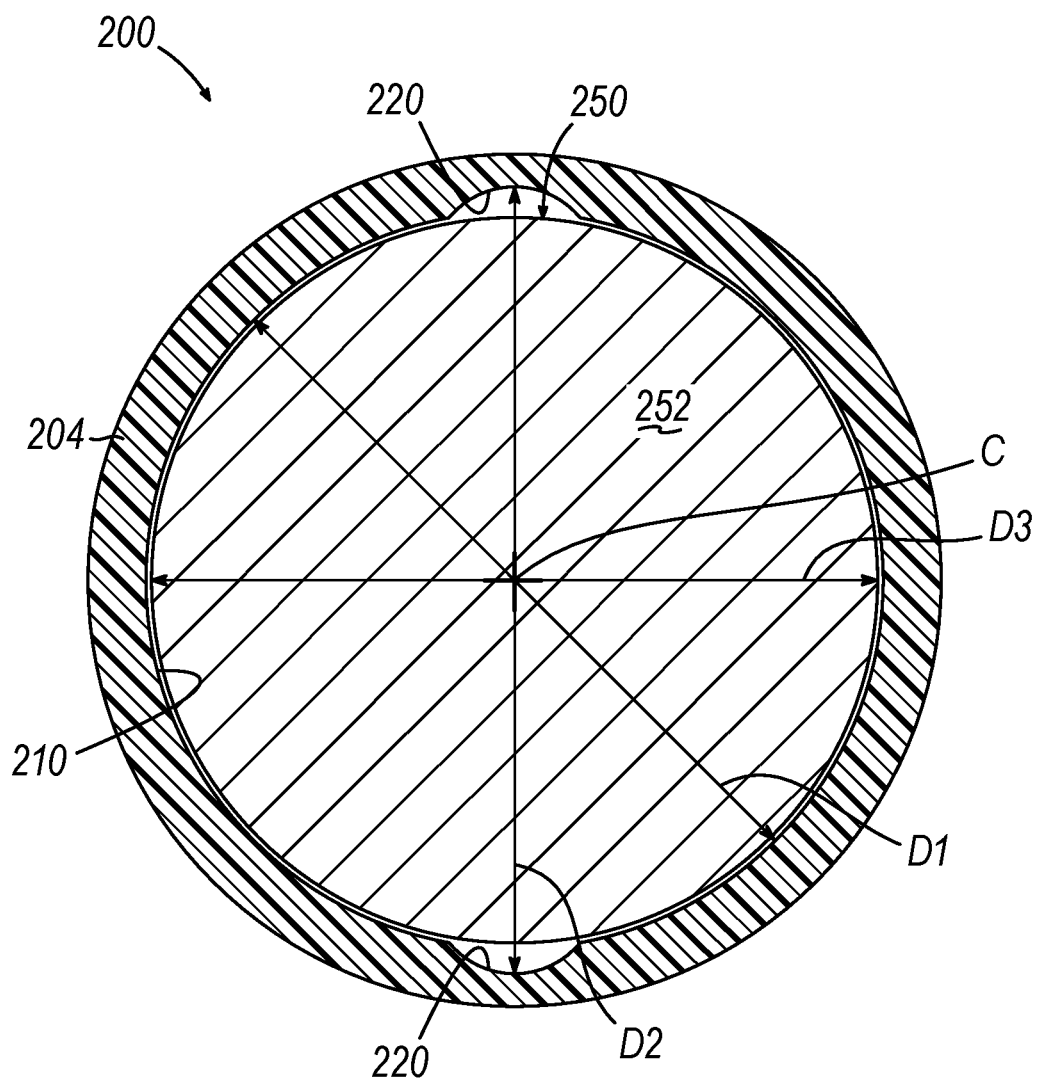
FIG. 7 depicts a top sectional view of the cannula of FIG. 6, taken along section line 7-7 in FIG. 6, showing a surgical instrument shaft disposed within a lumen of the cannula.
Figure 8:
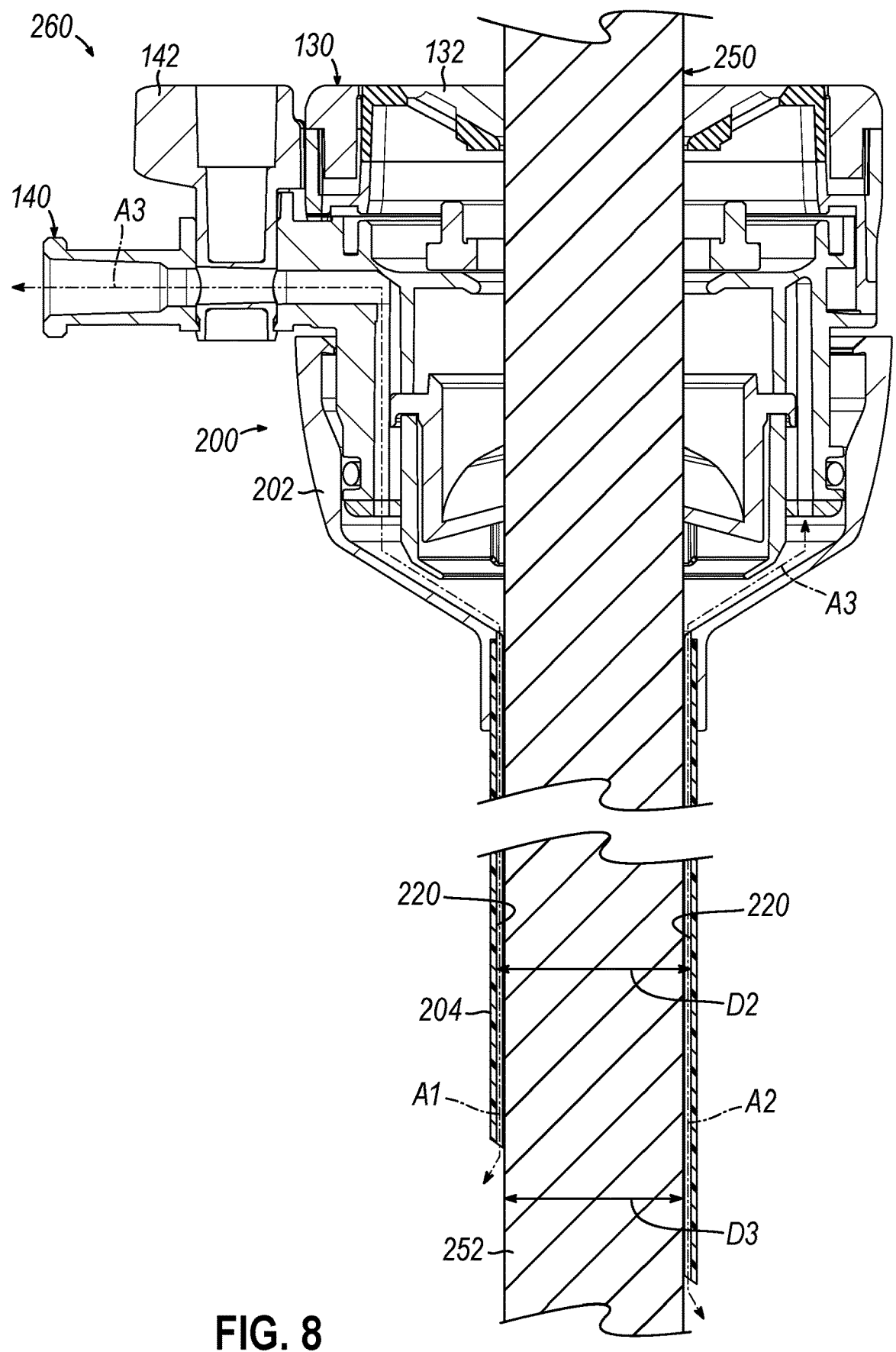
FIG. 8 depicts a side sectional view of an exemplary trocar that includes the cannula of FIG. 6, showing a surgical instrument shaft disposed within a working channel of the trocar, and showing exemplary flow of gas through the channels between an open distal end of the cannula and a proximally located insufflation port of the trocar.

FIGS. 6-8 show an exemplary cannula (200) configured to facilitate evacuation of smoke from abdominal cavity (1), as well as facilitate maintenance insufflation of abdominal cavity (1), even when a surgical instrument having a shaft of maximum permissible diameter is directed distally through cannula (200). Cannula (200) is similar to cannula (120) described above except as otherwise described below.

Cannula (200) includes a bell-shaped hub (202) at a proximal end, and an elongate cylindrical tube (204) extending distally from hub (202) and terminating at an angled distal tip (206). An outer surface of cannula tube (204) includes a plurality of tissue gripping features in the form of annular ribs (208) that are similar in structure and function to ribs (26, 128) described above. Cannula tube (204) includes a cylindrical inner surface (210) that defines a lumen (212) extending longitudinally along a central axis (C) through cannula (200). Cannula lumen (212) is configured to cooperate with a seal assembly (not shown), which may be similar to seal assembly (130) described above, to define a working channel of a corresponding trocar cannula assembly, such that cannula lumen (212) is configured to receive and guide a surgical instrument shaft distally therethrough and into the abdominal cavity (1) of a patient in which cannula tube (204) is positioned.

Unlike cannulas (20, 120) described above, cannula (200) of the present example includes a pair of gas flow channels (220) formed in cylindrical inner surface (210). As described in greater detail below in connection with FIGS. 7 and 8, gas flow channels (220) are configured to facilitate proximally-directed smoke evacuation from abdominal cavity (1), or alternatively distally-directed maintenance insufflation of abdominal cavity (1), during a surgical procedure while a surgical instrument shaft is disposed within cannula lumen (212). Gas flow channels (220) extend longitudinally between a proximal end of cannula lumen (212) that opens to an interior of cannula hub (202), and a distal end of cannula lumen (212) that opens through distal tip (206). In the present version, channels (220) are provided in a pair and are arranged at diametrically opposed positions, though it will be appreciated that channels (220) may be provided in various other quantities and arrangements in other versions, for example as described in greater detail below.

In the example shown, channels (220) each have a generally uniform transverse cross-sectional shape and size along their respective lengths. More particularly, and as best shown in FIG. 7, channels (220) of the present example each have a rounded, generally semi-circular transverse cross-sectional shape of uniform size along their respective lengths. It will be appreciated that channels (220) may be provided with various other uniform or non-uniform cross-sectional shapes and sizes in other versions, for example as described in greater detail below. In some examples, proximal ends of channels (220) may smoothly transition to a proximal face of cannula tube (204), such as via one or more radiuses or chamfers, to prevent interfering with distal insertion of surgical instrument shafts into lumen (212) (e.g., snagging). Channels (220) may be formed in inner surface (210) in any suitable manner, including via subtractive processes such as machining or broaching, stamping, or 3D printing.

As shown, channels (220) are each formed in inner surface (210) such that each channel (220) extends radially outwardly from inner surface (210) relative to central axis (C) into tube (204) and is in fluid communication with lumen (212), at least in the absence of any surgical instrument shaft in lumen (212). As a result, lumen (212) and channels (220) may collectively define a single continuous bore extending longitudinally between proximal and distal ends of cannula tube (204). Thus, channels (220) may be configured to at least partially define one or more gas flow path(s) through such a bore, irrespective of whether lumen (212) is occupied by a surgical instrument shaft and irrespective of a cross dimension of such a shaft. Such a gas flow path may be considered "persistent" since the path is maintained even when lumen (212) is fully occupied by a surgical instrument shaft.

In this regard, and as shown in FIG. 7, lumen (212) forms a first diameter (D1) and channels (220) collectively form a second effective diameter (D2) that extends through central axis (C) and is greater than first diameter (D1). First diameter (D1) of lumen (212) is sized to accommodate surgical instruments having shafts of various cross dimensions restricted to an upper limit or maximum permissible third diameter (D3) substantially equal to or slightly less than first diameter (D1) so that such shafts may be slidable within lumen (212) with a suitable degree of tolerance, including an exemplary surgical instrument (250) having a shaft (252) with such a maximum permissible third diameter (D3). Thus, shaft (252) may substantially occupy lumen (212) when surgical instrument (250) is positioned within the working channel of the corresponding trocar cannula assembly, and may consequently substantially obstruct flow of gas (e.g., smoke and/or insufflation gas) through lumen (212) in either a proximal or distal direction. Channels (220) may be configured to permit flow of such gas therethrough in either the proximal or distal direction while at least partially circumventing or bypassing lumen (212).

For example, in cases where third diameter (D3) of instrument shaft (252) is appreciably less than first diameter (D1) of lumen (212) such that shaft (252) only partially obstructs flow of gas through lumen (212), channels (220) and the unoccupied portion(s) of lumen (212) may collectively define a single, enlarged gas flow path extending longitudinally between proximal and distal ends of cannula tube (204) for improving flow of gas relative to a gas flow path defined by the unoccupied portion(s) of lumen (212) alone. In cases where third diameter (D3) of shaft (252) is substantially equal to first diameter (D1) of lumen (212) such that shaft (252) fully obstructs flow of gas through lumen (212), channels (220) may define discrete gas flow paths each extending longitudinally along an outer surface of shaft (252) between proximal and distal ends of cannula tube (204) for permitting flow of gas despite complete blockage of lumen (212).

More particularly, and as shown in FIG. 8, channels (220) may define first and second gas flow paths indicated by first and second arrows (A1, A2), respectively, each extending longitudinally along an outer surface of shaft (252) between proximal and distal ends of cannula tube (204). When cannula (200) is coupled to seal assembly (130) to form a cannula assembly (260), the first and second gas flow paths may converge together into a third gas flow path indicated by third arrows (A3) and collectively defined by an annular chamber and connecting passageways provided in and between cannula hub (202) and seal assembly (130). As shown, third gas flow path may pass outwardly through insufflation port (140) of seal assembly (130). In this regard, third gas flow path may be partially defined by a bore of a luer lock fitting (not shown) configured to couple with insufflation port (140) and in fluid communication with an insufflation fluid source and/or vacuum source. In one example, hub (202) may include notches (270) radially aligned with channels (220) for assisting in providing fluid communication between each of the first and second gas flow paths with the third gas flow path.

Each of the first, second, and third gas flow paths described above may be bidirectional to permit gas to be proximally-directed from the first and second flow paths to the third gas flow path and evacuated via insufflation port (140); and alternatively to permit gas to be introduced via insufflation port (140) and distally directed from the third flow path to the first and second flow paths. Thus, while cannula lumen (212) is occupied by surgical instrument shaft (252), undesirable fluids such as smoke may be directed proximally along the first, second, and third gas flow paths for evacuation from abdominal cavity (1), or an insufflation fluid such as carbon dioxide may be directed distally along the first, second, and third flow paths to provide maintenance insufflation of abdominal cavity (1). It will be appreciated that the proximal evacuation of smoke from abdominal cavity (1) and the distal supply of inflation gas to abdominal cavity (1) described above may be mutually exclusive actions, such that during procedure gas flow channels (220) may direct only one of smoke or insufflation gas therethrough at any selected point in time.

In this manner, gas flow channels (220) may allow third diameter (D3) of surgical instrument shaft (252) to be maximized relative to first diameter (D1) of cannula lumen (212) while maintaining at least one open gas flow path through the bore of cannula tube (204) for evacuation and/or insufflation. In other words, channels (220) may provide at least one gas flow path through the bore of cannula tube (204) without interfering with the size restrictions imposed on surgical instrument shaft (252) by first diameter (D1) of lumen (212). Thus, inner surface (210) of cannula tube (204) may remain configured to radially contact and constrain shaft (252) having maximum permissible third diameter (D3) at various contact points between channels (220) to thereby assist in centering shaft (252) relative to central axis (C) while the persistent first and second gas flow paths are maintained in an open state by channels (220).

In one example, gas flow channels (220) may be sized relative to the bores and/or passageways that define the third gas flow path such that the first and second gas flow paths are relatively unconstricted compared to third gas flow path and/or compared to other upstream/downstream flow paths in fluid communication therewith. For example, a bore of a luer lock fitting coupled with insufflation port (140) may define a greater fluid constriction than channels (220), even when lumen (212) is occupied by surgical shaft (252). Thus, fluids directed along the first, second, and third gas flow paths either proximally or distally may experience greater fluid constriction while traversing the third gas flow path and/or such other upstream/downstream flow paths than while traversing either of the first or second gas flow paths. In this manner, gasses may travel predictably and consistently between insufflation port (140) and the bore of cannula tube (204), including lumen (212) and gas flow channels (220), irrespective of whether lumen (212) is occupied by a surgical instrument shaft and irrespective of a cross dimension of such a shaft.

During operation, cannula (200) may be positioned at a desired depth of insertion in the patient's abdominal cavity (1) as described above with respect to FIGS. 3A and 3B to permit performance of a laparoscopic surgical procedure. The procedure may include distally inserting shaft (252) of surgical instrument (250) into cannula lumen (212) such that lumen (212) is at least partially occupied by shaft (252). In one example, the procedure may also include applying radio frequency (RF) energy and/or thermal energy to tissue via instrument (250), and evacuating smoke generated within abdominal cavity (1) by such energy application proximally through the bore of cannula tube (204) along the first, second, and third gas flow paths and outwardly through insufflation port (140). In another example, the procedure may include introducing insufflation fluid, such as carbon dioxide, via insufflation port (140) and directing such insufflation fluid distally through the third gas flow path and through the bore of cannula tube (204) along first and second gas flow paths into abdominal cavity (1) to facilitate maintenance of an insufflated state of abdominal cavity (1).

B. Alternative Gas Flow Channel Profiles and Arrangements

In some instances, it may be desirable to provide a cannula with gas flow channels provided in an inner cylindrical surface thereof in quantities and arrangements that differ from those of cannula (200) described above. Each of the exemplary cannulas (300, 400, 500, 600, 700, 800, 900, 1000) described below in connection to FIGS. 9-16 is configured to facilitate evacuation of smoke from abdominal cavity (1), as well as facilitate maintenance insufflation of abdominal cavity (1), even when a surgical instrument having a shaft of maximum permissible diameter is directed distally therethrough; and each is similar to cannula (200) described above except as otherwise described below.

Figure 9:
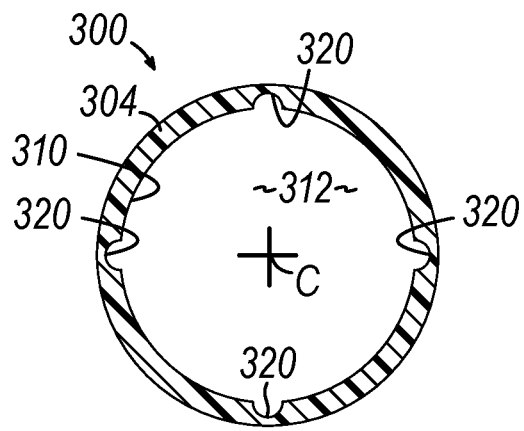
FIG. 9 depicts a top sectional view of another exemplary cannula tube having a plurality of gas flow channels formed in its cylindrical inner surface.

FIG. 9 shows a second exemplary cannula (300) which includes an elongate cylindrical tube (304) including a cylindrical inner surface (310) that defines a lumen (312) extending longitudinally along a central axis (C) through cannula (300). Cannula (300) also includes a plurality of gas flow channels (320) formed in cylindrical inner surface (310). In the present version, four channels (320) are arranged with uniform circumferential spacing about central axis (C). Channels (320) of the present example each have a rounded, generally semi-circular transverse cross-sectional shape. In this regard, the center points of the circular profiles defined by each channel (320) are positioned substantially on the circular profile defined by inner surface (310). In other words, the center points of the circular profiles defined by each channel (320) are positioned at a same radial distance from central axis (C) as the circular profile defined by inner surface (310).

Figure 10:
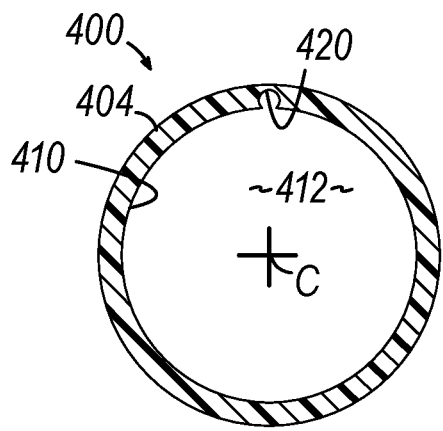
FIG. 10 depicts a top sectional view of another exemplary cannula tube having a single gas flow channel formed in its cylindrical inner surface.

FIG. 10 shows a third exemplary cannula (400) which includes an elongate cylindrical tube (404) including a cylindrical inner surface (410) that defines a lumen (412) extending longitudinally along a central axis (C) through cannula (400). Cannula (400) also includes a single gas flow channel (420) formed in cylindrical inner surface (410). Channel (420) of the present example has a rounded, generally C-shaped transverse cross-sectional shape. In this regard, the center point of the circular profile defined by channel (420) is positioned radially outwardly from the circular profile defined by inner surface (410) relative to central axis (C).

Figure 11:
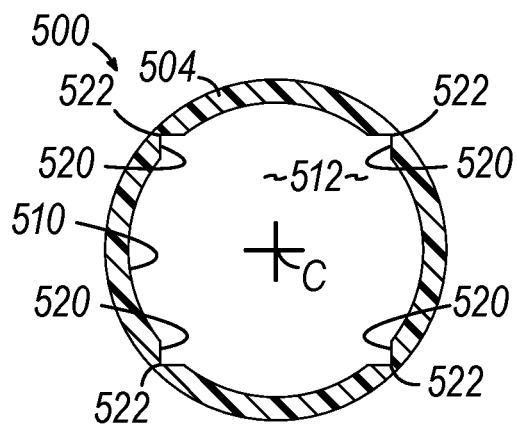
FIG. 11 depicts a top sectional view of another exemplary cannula tube having a plurality of gas flow channels formed in its cylindrical inner surface.

FIG. 11 shows a fourth exemplary cannula (500) which includes an elongate cylindrical tube (504) including a cylindrical inner surface (510) that defines a lumen (512) extending longitudinally along a central axis (C) through cannula (500). Cannula (500) also includes a plurality of gas flow channels (520) formed in cylindrical inner surface (510). In the present version, four channels (520) are arranged with uniform circumferential spacing about central axis (C). Channels (520) of the present example each have a sharp, generally L-shaped transverse cross-sectional shape. In this regard, each channel (520) includes an inside corner (522). As a result, channels (520) collectively have a generally square-shaped transverse cross-section.

Figure 12:
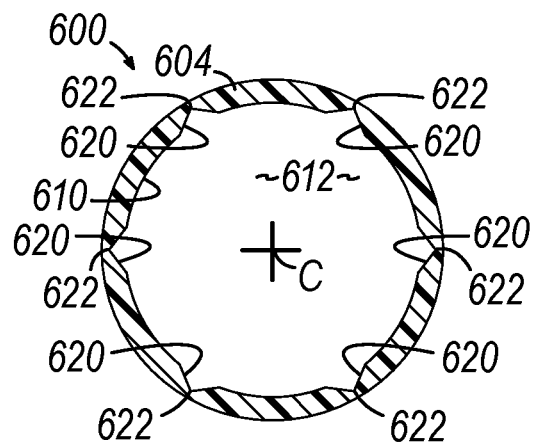
FIG. 12 depicts a top sectional view of another exemplary cannula tube having a plurality of gas flow channels formed in its cylindrical inner surface.

FIG. 12 shows a fifth exemplary cannula (600) which includes an elongate cylindrical tube (604) including a cylindrical inner surface (610) that defines a lumen (612) extending longitudinally along a central axis (C) through cannula (600). Cannula (600) also includes a plurality of gas flow channels (620) formed in cylindrical inner surface (610). In the present version, six channels (620) are arranged with uniform circumferential spacing about central axis (C). Channels (620) of the present example each have a sharp, generally obtusely bent L-shaped transverse cross-sectional shape. In this regard, each channel (620) includes an inside corner (622). As a result, channels (620) collectively have a generally hexagon-shaped transverse cross-section.

Figure 13:
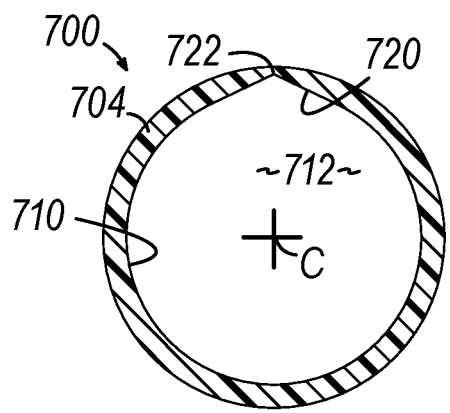
FIG. 13 depicts a top sectional view of another exemplary cannula tube having a single gas flow channel formed in its cylindrical inner surface.

FIG. 13 shows a sixth exemplary cannula (700) which includes an elongate cylindrical tube (704) including a cylindrical inner surface (710) that defines a lumen (712) extending longitudinally along a central axis (C) through cannula (700). Cannula (700) also includes a single gas flow channel (720) formed in cylindrical inner surface (710). Channel (720) of the present example has a sharp, generally obtusely bent L-shaped transverse cross-sectional shape. In this regard, channel (720) intersects with inner surface (710) generally tangentially and includes an inside corner (722). As a result, channel (720) and lumen (712) collectively have a generally teardrop-shaped transverse cross-section.

Figure 14:
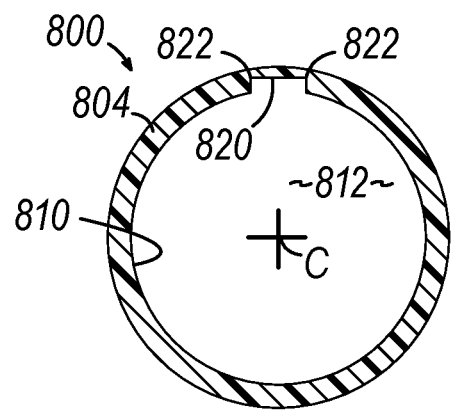
FIG. 14 depicts a top sectional view of another exemplary cannula tube having a single gas flow channel formed in its cylindrical inner surface.

FIG. 14 shows a seventh exemplary cannula (800) which includes an elongate cylindrical tube (804) including a cylindrical inner surface (810) that defines a lumen (812) extending longitudinally along a central axis (C) through cannula (800). Cannula (800) also includes a single gas flow channel (820) formed in cylindrical inner surface (810). Channel (820) of the present example has a generally rectangular keyway-shaped transverse cross-sectional shape. In this regard, channel (820) includes a pair of inside corners (822).

Figure 15:
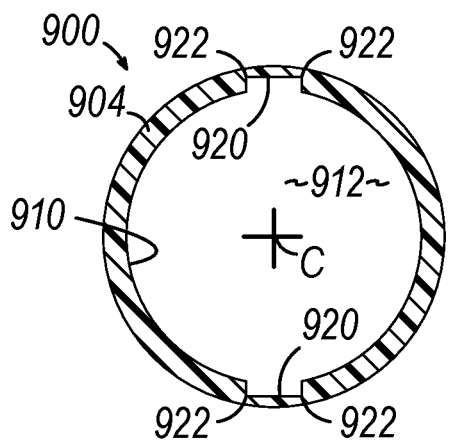
FIG. 15 depicts a top sectional view of another exemplary cannula tube having a plurality of gas flow channels formed in its cylindrical inner surface.

FIG. 15 shows an eighth exemplary cannula (900) which includes an elongate cylindrical tube (904) including a cylindrical inner surface (910) that defines a lumen (912) extending longitudinally along a central axis (C) through cannula (900). Cannula (900) also includes a plurality of gas flow channels (920) formed in cylindrical inner surface (910). In the present version, channels (920) are provided in a pair and are arranged at diametrically opposed positions. Channels (920) of the present example each have a generally rectangular keyway-shaped transverse cross-sectional shape. In this regard, channels (920) each include a pair of inside corners (922).

Figure 16:
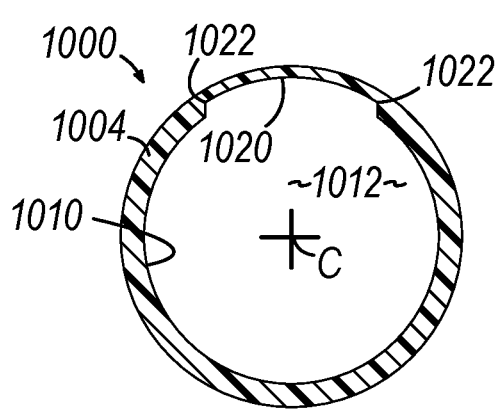
FIG. 16 depicts top sectional view of another exemplary cannula tube having a single gas flow channel formed in its cylindrical inner surface.

FIG. 16 shows a ninth exemplary cannula (1000) which includes an elongate cylindrical tube (1004) including a cylindrical inner surface (1010) that defines a lumen (1012) extending longitudinally along a central axis (C) through cannula (1000). Cannula (1000) also includes a single gas flow channel (1020) formed in cylindrical inner surface (1010). Channel (1020) of the present example has a generally circumferentially extending slot-shaped transverse cross-sectional shape. In this regard, channel (820) includes a pair of inside corners (1022).

C. Cannula Having Gas Flow Channels with Larger Proximal End Widths Than Distal End Widths In some instances, it may be desirable to configure a trocar cannula such that it is resistant to unwanted tipping, or tilting, relative to the abdominal wall (2) of a patient when the corresponding cannula assembly is temporarily released by the surgeon, such that the cannula assembly remains axially aligned with the surgical site throughout a procedure. Each of the exemplary cannulas (1100, 1200) described below in connection with FIGS. 17-21 is similar to cannula (200) described above except as otherwise described below. For example, each of the exemplary cannulas (1100, 1200) described below includes gas flow channels that are constructed so as to position the center of mass, and thus center of gravity, of cannula (1100, 1200) further distally along cannula tube (1104, 1204) compared to cannulas (200, 300, 400, 500, 600, 700, 800, 900, 1000) described above. Advantageously, this distal relocation of the center of gravity effectively reduces the "tipping" torque that it exerts about the portion of cannula (1100, 1200) positioned within abdominal wall (2), which acts as a pivot point, thereby reducing unwanted tipping of cannula (1100, 1200) when released by the surgeon.

1. Cannula Having Tapered Gas Flow Channels

Figure 17:
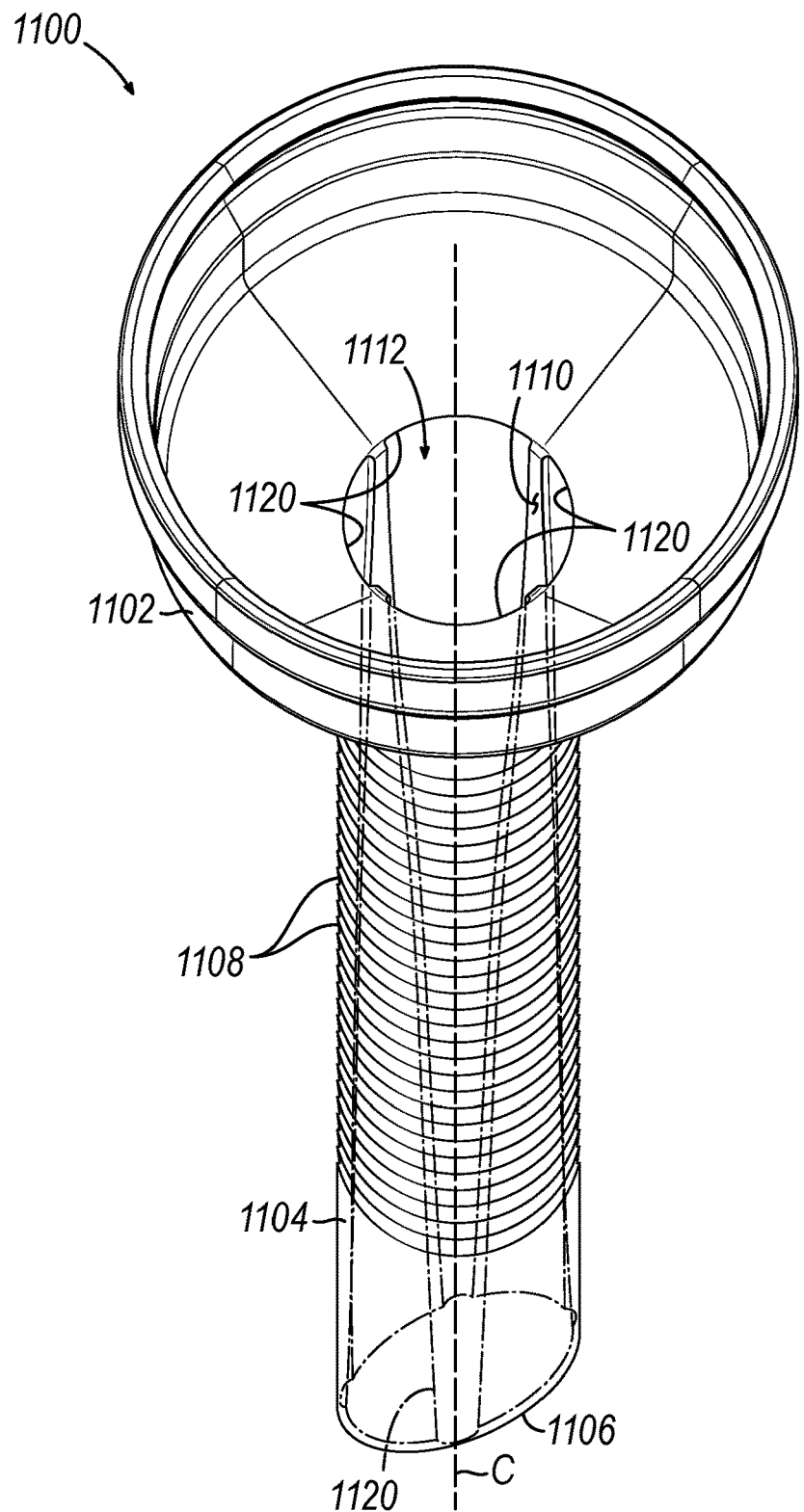
FIG. 17 depicts a perspective view of another exemplary cannula having a plurality of tapered gas flow channels formed in a cylindrical inner surface of the cannula tube.
Figure 18:
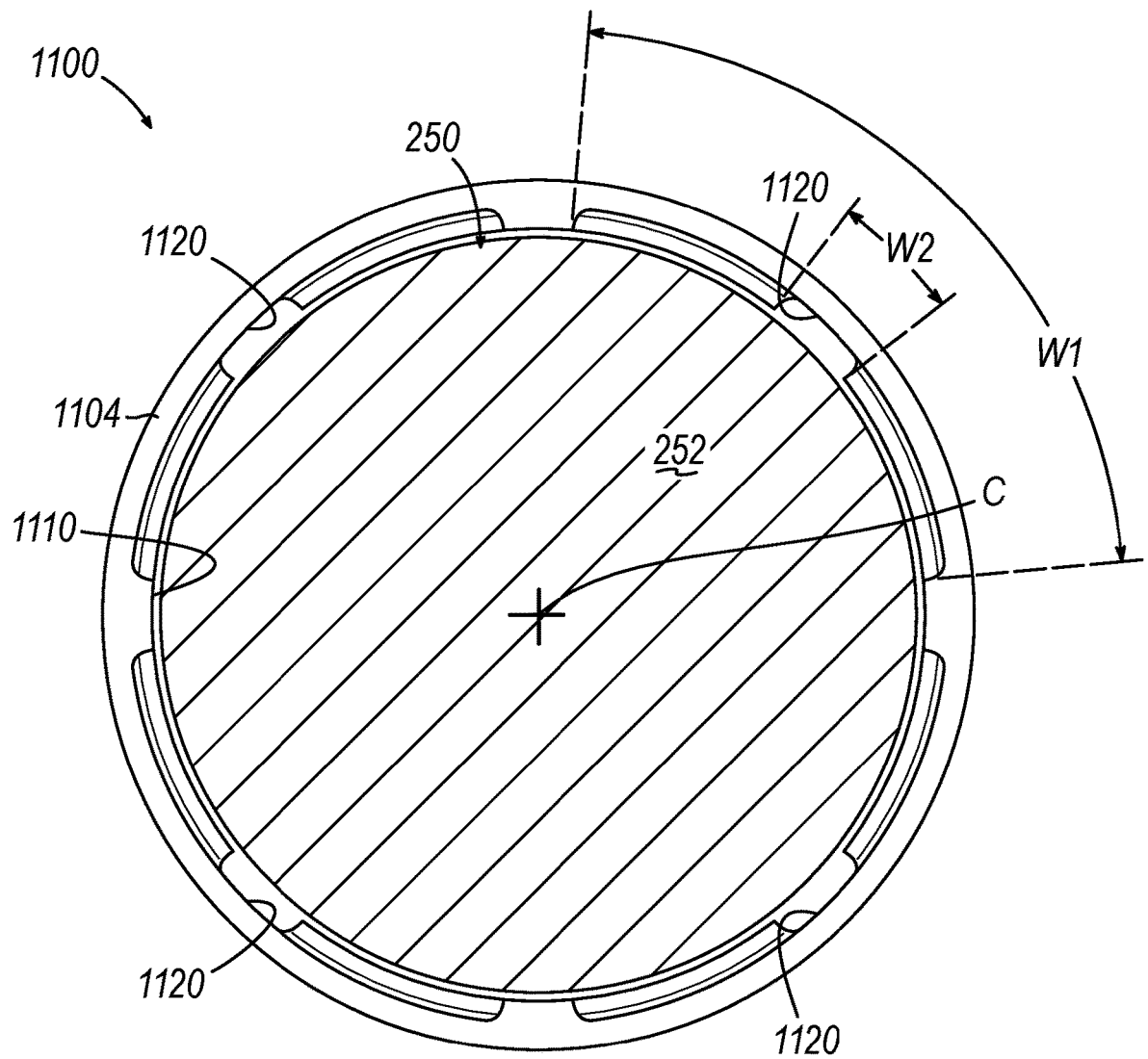
FIG. 18 depicts a top elevational view of the cannula tube of FIG. 17, showing a surgical instrument shaft disposed within a lumen of the cannula tube.

FIGS. 17-18 show a tenth exemplary cannula (1100) which includes a bell-shaped hub (1102) at a proximal end, and an elongate cylindrical tube (1104) extending distally from hub (1102) and terminating at an angled distal tip (1106). An outer surface of cannula tube (1104) includes a plurality of tissue gripping features in the form of annular ribs (1108) that are similar in structure and function to ribs (26, 128) described above. Cannula tube (1104) includes a cylindrical inner surface (1110) that defines a lumen (1112) extending longitudinally along a central axis (C) through cannula (1100).

Cannula (1100) also includes a plurality of gas flow channels (1120) formed in cylindrical inner surface (1110). Gas flow channels (1120) are configured to facilitate proximally-directed smoke evacuation from abdominal cavity (1), or alternatively distally-directed maintenance insufflation of abdominal cavity (1), during a surgical procedure while a surgical instrument shaft is disposed within cannula lumen (1112) in manners similar to those described above in connection with FIGS. 6-8. Gas flow channels (1120) extend longitudinally between a proximal end of cannula lumen (1112) that opens to an interior of cannula hub (1102), and a distal end of cannula lumen (1112) that opens through distal tip (1106). In the present version, four channels (1120) are arranged with uniform circumferential spacing about central axis (C), though it will be appreciated that channels (1120) may be provided in various other quantities and arrangements in other versions, for example as described in greater detail below.

In the example shown, channels (1120) each have a generally non-uniform transverse cross-sectional shape and/or size along their respective lengths. More particularly, channels (1120) of the present example each have a generally circumferentially extending slot-shaped transverse cross-sectional shape of non-uniform size along their respective lengths. In this regard, and as best shown in FIG. 18, channels (1120) each include a proximal end having a first circumferential width (W1) and a distal end having a second circumferential width (W2) less than the first width (W1). In the present example, each channel (1120) tapers circumferentially inwardly in a distal direction from a circumferentially widest portion of channel (1120) at the proximal end thereof to a circumferentially narrowest portion of channel (1120) at the distal end thereof In other words, a width of each channel (1120) tapers distally and uniformly from the proximal end of channel (1120) to the distal end of channel (1120). It will be appreciated that channels (1120) may be provided with various other non-uniform cross-sectional shapes and/or sizes in other versions which result in an increased sizing (e.g., widening) of channels (1120) at proximal ends thereof relative to distal ends thereof, for example as described in greater detail below.

Such increased sizing of each channel (1120) at the proximal end thereof relative to the distal end thereof may allow cannula tube (1104) to include a relatively reduced amount of material at or near the proximal end thereof and a relatively increased amount of material at or near the distal end thereof. As a result, the weight distribution of cannula (1100) may be shifted distally such that the center of mass, and thus center of gravity, of cannula (1100) may be located further distally along cannula tube (1104) compared to cannulas (200, 300, 400, 500, 600, 700, 800, 900, 1000) described above. In this manner, channels (1120) may be configured to effectively reduce the "tipping" torque exerted by cannula (1100) about the portion of cannula (1100) positioned within abdominal wall (2), and to thereby reduce unwanted tipping of cannula (1100) when released by the surgeon.

During operation, cannula (1100) may be positioned at a desired depth of insertion in the patient's abdominal cavity (1) as described above with respect to FIGS. 3A and 3B to permit performance of a laparoscopic surgical procedure. The procedure may include distally inserting shaft (252) of surgical instrument (250) into lumen (1112) such that lumen (1112) is at least partially occupied by shaft (252). In one example, the procedure may also include evacuating smoke generated within abdominal cavity (1) by radio frequency (RF) energy and/or thermal energy application to tissue as described above with respect to FIG. 8. In another example, the procedure may include introducing insufflation fluid, such as carbon dioxide, into abdominal cavity (1) to facilitate maintenance of an insufflated state of abdominal cavity (1) as described above with respect to FIG. 8. In any case, the relatively distal center of gravity of cannula (1100) may be positioned at or near the abdominal wall (2) of the patient (e.g., the effective pivot point of cannula 1100) and thereby resist unwanted tipping to allow the corresponding cannula assembly to remain axially aligned with the surgical site throughout performance of the laparoscopic surgical procedure, even in instances when the surgeon may at least temporarily release the cannula assembly.

2. Cannula Having Stepped Gas Flow Channels

Figure 19:
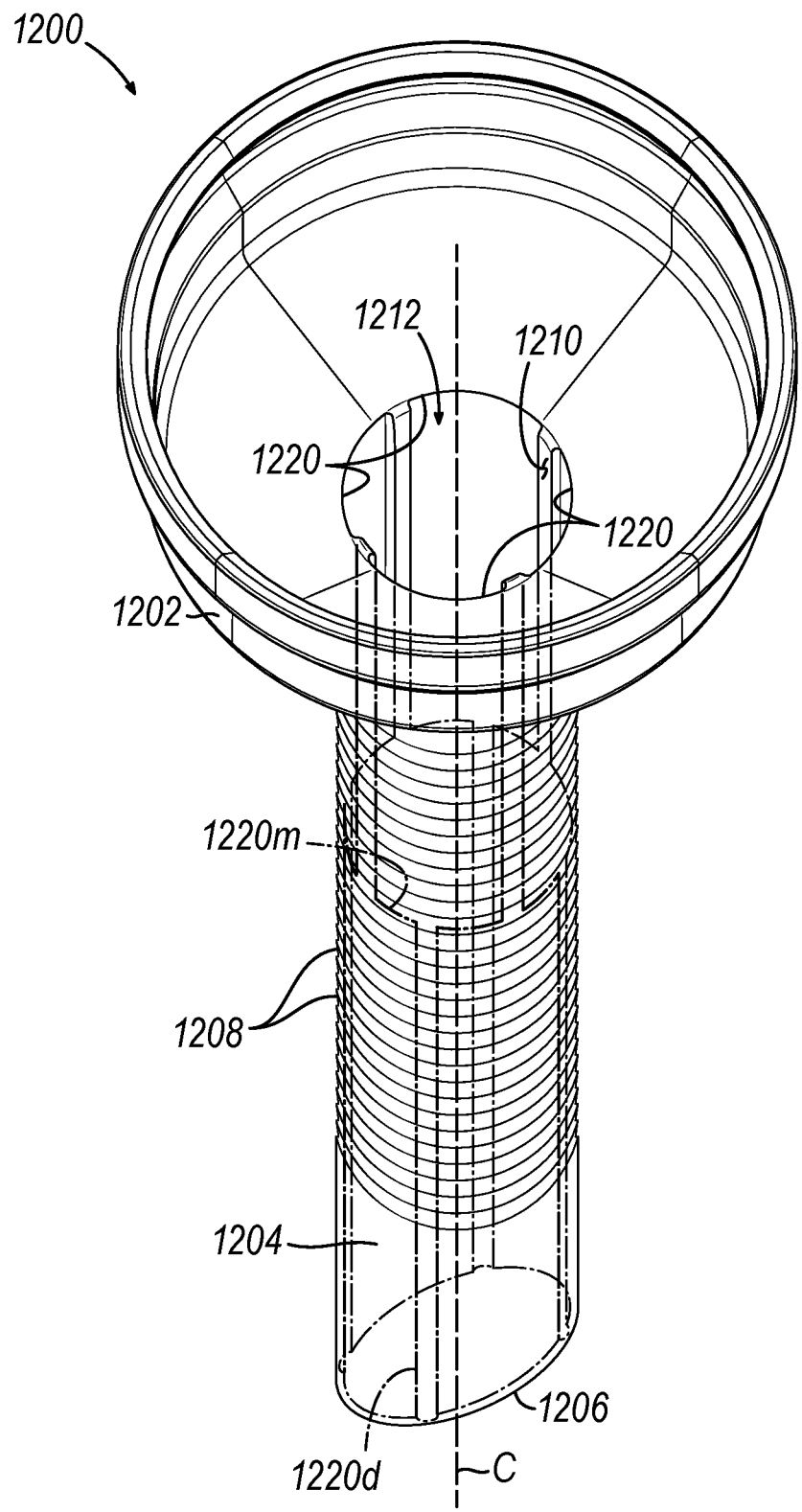
FIG. 19 depicts a perspective view of another exemplary cannula having a plurality of stepped gas flow channels formed in a cylindrical inner surface of the cannula tube.
Figure 21:
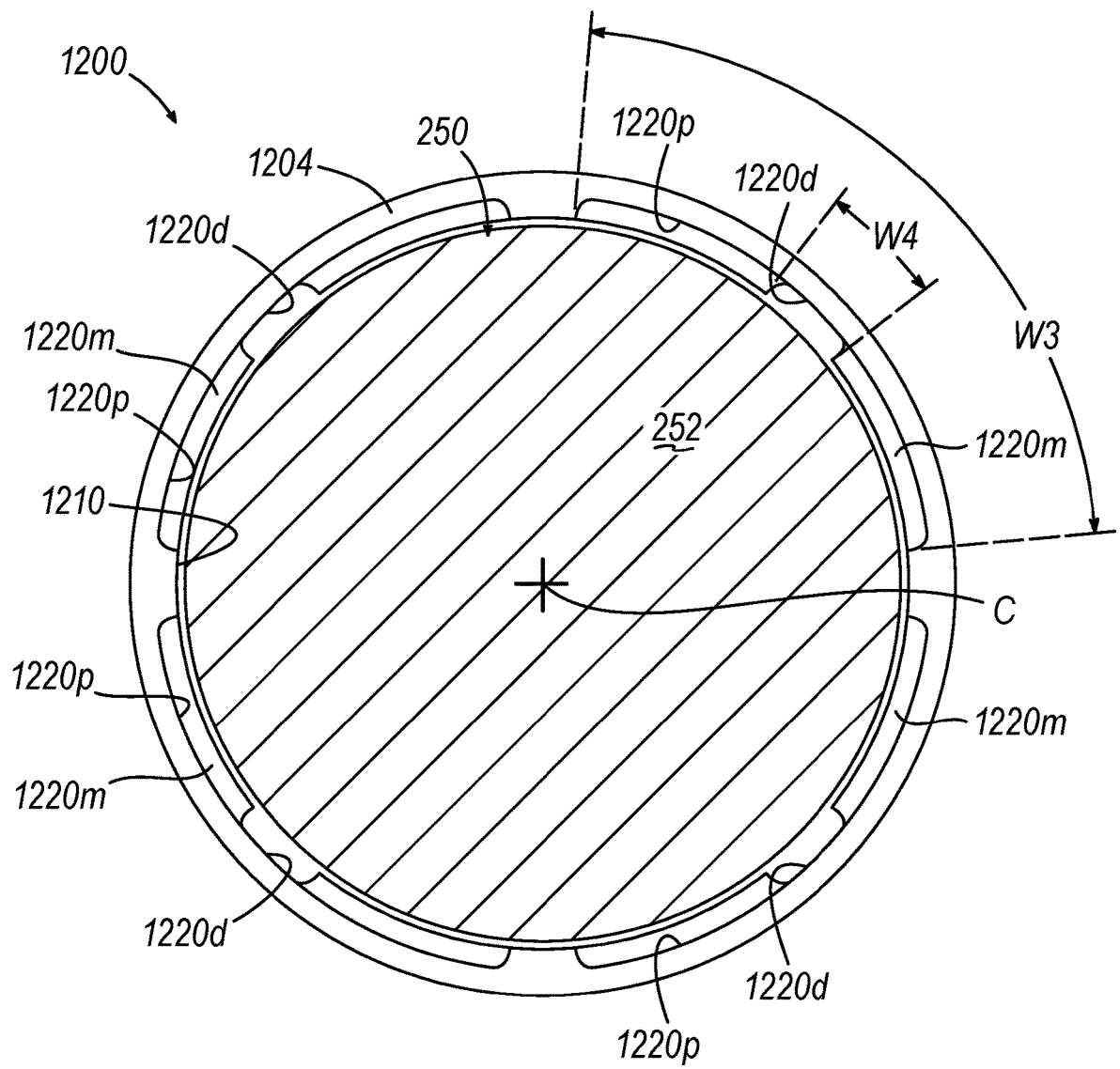
FIG. 21 depicts a top elevational view of the cannula tube of FIG. 19, showing a surgical instrument shaft disposed within a lumen of the cannula tube.

FIGS. 19-21 show an eleventh exemplary cannula (1200) which includes a bell-shaped hub (1202) at a proximal end, and an elongate cylindrical tube (1204) extending distally from hub (1202) and terminating at an angled distal tip (1206). An outer surface of cannula tube (1204) includes a plurality of tissue gripping features in the form of annular ribs (1208) that are similar in structure and function to ribs (26, 128) described above. Cannula tube (1204) includes a cylindrical inner surface (1210) that defines a lumen (1212) extending longitudinally along a central axis (C) through cannula (1200).

Cannula (1200) also includes a plurality of gas flow channels (1220) formed in cylindrical inner surface (1210). Gas flow channels (1220) are configured to facilitate proximally-directed smoke evacuation from abdominal cavity (1), or alternatively distally-directed maintenance insufflation of abdominal cavity (1), during a surgical procedure while a surgical instrument shaft is disposed within cannula lumen (1212) in manners similar to those described above in connection with FIGS. 6-8, and are further configured to effectively reduce the "tipping" torque exerted by cannula (1200) about the portion of cannula (1200) positioned within abdominal wall (2) in a manner similar to that described above in connection with FIGS. 17-18. Gas flow channels (1220) extend longitudinally between a proximal end of cannula lumen (1212) that opens to an interior of cannula hub (1202), and a distal end of cannula lumen (1212) that opens through distal tip (1206). In the present version, four channels (1220) are arranged with uniform circumferential spacing about central axis (C), though it will be appreciated that channels (1220) may be provided in various other quantities and arrangements in other versions, for example as described in greater detail below.

In the example shown, channels (1220) each have a generally non-uniform transverse cross-sectional shape and/or size along their respective lengths. More particularly, channels (1220) of the present example each have a generally circumferentially extending slot-shaped transverse cross-sectional shape of non-uniform size along their respective lengths. In this regard, and as best shown in FIGS. 20B and 21, channels (1220) each include a proximal channel portion (1220$p$) having a third uniform circumferential width (W3) along a length thereof and a distal channel portion (1220$d$) having a fourth uniform circumferential width (W4) along a length thereof and less than the third width (W3). In the present example, each channel (1220) further includes a medial channel portion (1220$m$) defining a stepped transition between proximal channel portion (1220$p$) and distal channel portion (1220$d$) such that each channel (1220) steps circumferentially inwardly in a distal direction from a circumferentially widest portion of channel (1120) at the proximal end thereof to a circumferentially narrowest portion of channel (1120) at the distal end thereof.

While the illustrated medial channel portions (1220$m$) each define a stepped transition between the respective proximal channel portion (1220$p$) and distal channel portion (1220$d$), it will be appreciated that some or all of medial channel portions (1220m) may alternatively define a tapered transition between the respective proximal channel portion (1220$p$) and distal channel portion (1220$d$). In the present version, a single medial channel portion (1220$m$) is provided for each channel (1220), though it will be appreciated that multiple medial channel portions (1220$m$) may be provided in other versions to define a multi-stage stepped and/or tapered transition between proximal portion (1220$p$) and distal channel portion (1220$d$).

Similar to cannula (1100), the increased sizing of each channel (1220) at the proximal end thereof relative to the distal end thereof may allow cannula tube (1204) to include a relatively reduced amount of material at or near the proximal end thereof and a relatively increased amount of material at or near the distal end thereof. As a result, the weight distribution of cannula (1200) may be shifted distally such that the center of mass, and thus center of gravity, of cannula (1200) may be located further distally along cannula tube (1204) compared to cannulas (200, 300, 400, 500, 600, 700, 800, 900, 1000) described above. In this manner, channels (1220) may be configured to effectively reduce the "tipping" torque exerted by cannula (1200) about the portion of cannula (1200) positioned within abdominal wall (2), and to thereby reduce unwanted tipping of cannula (1200) when released by the surgeon.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical access device comprising: (a) a proximal end portion configured to support a seal assembly having an insufflation port; (b) a cannula tube extending distally from the proximal end portion and having an inner surface that defines a lumen extending longitudinally through the cannula tube, wherein the cannula tube is configured to be inserted distally through a body cavity wall of a patient, wherein the lumen is configured to guide a surgical instrument shaft distally through the cannula tube for accessing a body cavity of the patient; and (c) at least one channel formed in the inner surface of the cannula tube, wherein the at least one channel extends longitudinally between a proximal end of the lumen and a distal end of the lumen, wherein the at least one channel is configured to direct a gas therethrough at least one of to or from the insufflation port of the seal assembly while a surgical instrument shaft is disposed within the lumen.

EXAMPLE 2

The surgical access device of Example 1, wherein the inner surface is cylindrical.

EXAMPLE 3

The surgical access device of any of the preceding Examples, wherein the at least one channel fluidly communicates with the lumen at least while the surgical instrument shaft is disposed outside of the lumen.

EXAMPLE 4

The surgical access device of any of the preceding Examples, wherein a proximal end of the at least one channel has a greater width than a distal end of the at least one channel.

EXAMPLE 5

The surgical access device of Example 4, wherein a width of the at least one channel tapers distally.

EXAMPLE 6

The surgical access device of Example 5, wherein the width tapers uniformly from a proximal end of the at least one channel to a distal end of the at least one channel.

EXAMPLE 7

The surgical access device of any one or more of Examples 1 through 3, wherein the at least one channel includes a proximal channel portion and a distal channel portion, wherein the proximal channel portion has a first uniform width along a length thereof, wherein the distal channel portion has a second uniform width along a length thereof, wherein the first and second uniform widths are different from each other.

EXAMPLE 8

The surgical access device of Example 7, wherein the first uniform width is greater than the second uniform width.

EXAMPLE 9

The surgical access device of any one or more of Examples 7 through 8, wherein the at least one channel further includes a medial channel portion between the proximal channel portion and the distal channel portion, wherein the medial channel portion defines at least one of a stepped transition or a tapered transition between the proximal channel portion and the distal channel portion.

EXAMPLE 10

The surgical access device of any of the preceding Examples, wherein the at least one channel comprises first and second channels.

EXAMPLE 11

The surgical access device of Example 10, wherein the second channel is diametrically opposed from the first channel.

EXAMPLE 12

The surgical access device of Example 10, wherein the at least one channel further comprises a third channel, wherein the first, second, and third channels are arranged with uniform circumferential spacing about a central axis of the lumen.

EXAMPLE 13

The surgical access device of any of the preceding Examples, wherein the at least one channel has a rounded transverse cross-sectional profile.

EXAMPLE 14

The surgical access device of any one or more of Examples 1 through 12, wherein the at least one channel includes at least one inside corner.

EXAMPLE 15

The surgical access device of any of the preceding Examples, further comprising at least one tissue engagement feature disposed along an outer surface of the cannula tube, wherein the tissue engagement feature is configured to stabilize the cannula tube relative to the body cavity wall of the patient when the cannula tube is inserted distally through the body cavity wall.

EXAMPLE 16

A surgical access device comprising: (a) a proximal end portion configured to support a seal assembly having an insufflation port; (b) a cannula tube extending distally from the proximal end portion and having an inner surface that defines a lumen, wherein the lumen is configured to guide a surgical instrument shaft distally through the cannula tube for accessing a body cavity of a patient; and (c) a channel formed in the cannula tube radially outwardly of the inner surface, wherein the channel extends longitudinally between a proximal end of the lumen and a distal end of the lumen, wherein the channel is configured to direct a gas therethrough at least one of to or from the insufflation port of the seal assembly while a surgical instrument shaft is disposed within the lumen.

EXAMPLE 17

The surgical access device of Example 16, wherein the channel fluidly communicates with the lumen at least while the surgical instrument shaft is disposed outside of the lumen.

EXAMPLE 18

The surgical access device of any one or more of Examples 16 through 17, wherein a proximal end of the channel has a greater width than a distal end of the channel.

EXAMPLE 19

A surgical access device comprising: (a) a proximal hub; (b) a seal assembly coupled with the proximal hub and having an insufflation port; (c) a cannula tube extending distally from the proximal hub and having a lumen configured to guide a surgical instrument shaft distally through the cannula tube for accessing a body cavity of a patient, wherein the lumen has a first diameter; and (d) a plurality of channels formed in the cannula tube and extending longitudinally between a proximal end of the lumen and a distal end of the lumen, wherein each channel is configured to direct gas therethrough at least one of to or from the insufflation port of the seal assembly while a surgical instrument shaft is disposed within the lumen, wherein the channels collectively define a second diameter that extends through a central axis of the lumen and is larger than the first diameter.

EXAMPLE 20

The surgical access device of Example 19, wherein each channel fluidly communicates with the lumen at least while the surgical instrument shaft is disposed outside of the lumen.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/0338273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, issued as U.S. Pat. No. 11,712,267 on Aug. 1, 2023; U.S. patent application Ser. No. 17/213,431, entitled "Two Piece Separable Obturator," filed on Mar. 26, 2021, published as U.S. Pat. Pub. No. 2021/0338275 on Nov. 4, 2021; U.S. patent application Ser. No. 17/213,434, entitled "Latchless Obturator with Interference Fit Feature," filed on Mar. 26, 2021, published as U.S. Pub. No. 2021/0338269 on Nov. 4, 2021; U.S. patent application Ser. No. 17/213,437, entitled "Balancing Feature for Reusable Trocar," filed on Mar. 26, 2021, issued as U.S. Pat. No. 11,559,329 on Jan. 24, 2023; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical access device comprising:
   (a) a proximal end portion configured to support a seal assembly having an insufflation port;
   (b) a cannula tube extending distally from the proximal end portion and having an inner surface that defines a lumen extending longitudinally through the cannula tube, wherein the cannula tube is configured to be inserted distally through a body cavity wall of a patient, wherein the lumen is configured to guide a surgical instrument shaft distally through the cannula tube for accessing a body cavity of the patient; and
   (c) at least one channel formed in the inner surface of the cannula tube, wherein the at least one channel extends longitudinally between a proximal end of the lumen and a distal end of the lumen, wherein the at least one channel is configured to direct a gas therethrough at least one of to or from the insufflation port of the seal assembly while a surgical instrument shaft is disposed within the lumen, wherein the at least one channel includes a proximal channel portion, a distal channel portion, and a medial channel portion positioned between the proximal channel portion and the distal channel portion, wherein the proximal channel portion has a first uniform width along a length thereof, wherein the distal channel portion has a second uniform width along a length thereof, wherein the first and second uniform widths are different from each other, wherein the medial channel portion defines a stepped transition between the proximal channel portion and the distal channel portion.

2. The surgical access device of claim 1, wherein the inner surface is cylindrical.

3. The surgical access device of claim 1, wherein the at least one channel fluidly communicates with the lumen at least while the surgical instrument shaft is disposed outside of the lumen.

4. The surgical access device of claim 1, wherein a proximal end of the at least one channel has a greater width than a distal end of the at least one channel.

5. The surgical access device of claim 1, wherein the first uniform width is greater than the second uniform width.

6. The surgical access device of claim 1, wherein the at least one channel comprises first and second channels.

7. The surgical access device of claim 6, wherein the second channel is diametrically opposed from the first channel.

8. The surgical access device of claim 6, wherein the at least one channel further comprises a third channel, wherein the first, second, and third channels are arranged with uniform circumferential spacing about a central axis of the lumen.

9. The surgical access device of claim 1, wherein the at least one channel has a rounded transverse cross-sectional profile.

10. The surgical access device of claim 1, wherein the at least one channel includes at least one inside corner.

11. The surgical access device of claim 1, further comprising at least one tissue engagement feature disposed along an outer surface of the cannula tube, wherein the tissue engagement feature is configured to stabilize the cannula tube relative to the body cavity wall of the patient when the cannula tube is inserted distally through the body cavity wall.

12. The surgical access device of claim 1, wherein the proximal channel portion, the medial channel portion, and the distal channel portion are defined by the inner surface of the cannula tube.

13. A surgical access device comprising:
   (a) a proximal end portion configured to support a seal assembly having an insufflation port;
   (b) a cannula tube extending distally from the proximal end portion and having an inner surface that defines a lumen, wherein the lumen is configured to guide a surgical instrument shaft distally through the cannula tube for accessing a body cavity of a patient; and
   (c) a channel formed in the cannula tube radially outwardly of the inner surface, wherein the channel extends longitudinally between a proximal end of the lumen and a distal end of the lumen, wherein the channel is configured to direct a gas therethrough at least one of to or from the insufflation port of the seal assembly while a surgical instrument shaft is disposed within the lumen, wherein the channel includes a proximal channel portion, a distal channel portion, and a medial channel portion positioned between the proximal channel portion and the distal channel portion, wherein the medial channel portion defines a stepped transition between the proximal channel portion and the distal channel portion.

14. The surgical access device of claim 13, wherein the channel fluidly communicates with the lumen at least while the surgical instrument shaft is disposed outside of the lumen.

15. The surgical access device of claim 13, wherein a proximal end of the channel has a greater width than a distal end of the channel.

16. The surgical access device of claim 13, wherein the proximal channel portion has a first uniform circumferential width along a length thereof, wherein the distal channel portion has a second uniform circumferential width along a length thereof.

17. The surgical access device of claim 13, wherein the cannula tube defines a longitudinal axis that extends distally away from the proximal end portion, wherein the stepped transition transversely extends relative to the longitudinal axis.

18. A surgical access device comprising:
   (a) a proximal hub;
   (b) a seal assembly coupled with the proximal hub and having an insufflation port;
   (c) a cannula tube extending distally from the proximal hub and having a lumen configured to guide a surgical instrument shaft distally through the cannula tube for accessing a body cavity of a patient, wherein the lumen has a first diameter;
   (d) a plurality of channels defined by an inner surface of the cannula tube and extending longitudinally between a proximal end of the lumen and a distal end of the lumen, wherein each of the plurality of channels is configured to direct gas therethrough at least one of to or from the insufflation port of the seal assembly while a surgical instrument shaft is disposed within the lumen, wherein the plurality of channels collectively define a second diameter that extends through a central axis of the lumen and is larger than the first diameter, wherein each of the plurality of channels tapers from its proximal end to its distal end, wherein the proximal end includes a first circumferential width and the distal end includes a second circumferential width, wherein the second circumferential width is lesser than the first circumferential width; and (e) a plurality of raised inner portions defined by the cannula tube, wherein each of the plurality of raised inner portions includes a first radial thickness extending in a direction transverse to the central axis from the inner surface of the cannula tube to an outer surface of the cannula tube, wherein the plurality of channels includes a second radial thickness extending in a direction transverse to the central axis, wherein the second radial thickness is less than the first radial thickness.

19. The surgical access device of claim 18, wherein each of the plurality of channels fluidly communicates with the lumen at least while the surgical instrument shaft is disposed outside of the lumen.

20. The surgical access device of claim 18, wherein each of the plurality of channels is defined by the plurality of raised inner portions of the cannula tube wherein the plurality of raised inner portions of the cannula tube include a pair of raised inner portions defining each of the plurality of channels, wherein each of the plurality of raised inner portions includes a proximal cylindrical width and a distal cylindrical width, wherein the distal cylindrical width is greater than the proximal cylindrical width.

* * * * *